(12) United States Patent
Ciszkowski et al.

(10) Patent No.: US 10,263,871 B2
(45) Date of Patent: Apr. 16, 2019

(54) ADVERSE EVENT DATA CAPTURE AND ALERT SYSTEMS AND METHODS

(71) Applicant: Purdue Pharma L.P., Stamford, CT (US)

(72) Inventors: Mietek Ciszkowski, Milford, CT (US); Larry Egan, Brookfield, CT (US); Sayee Natarajan, Norwalk, CT (US); Larry Pickett, Mahwah, NJ (US); Jake Stahl, Milford, CT (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/196,564

(22) Filed: Mar. 4, 2014

(65) Prior Publication Data

US 2014/0250224 A1 Sep. 4, 2014

Related U.S. Application Data

(63) Continuation of application No. 11/925,403, filed on Oct. 26, 2007, now Pat. No. 8,666,764.

(60) Provisional application No. 60/867,923, filed on Nov. 30, 2006, provisional application No. 60/863,243, filed on Oct. 27, 2006.

(51) Int. Cl.
*G06F 19/00* (2018.01)
*H04L 12/26* (2006.01)

(52) U.S. Cl.
CPC .......... *H04L 43/10* (2013.01); *G06F 19/3456* (2013.01)

(58) Field of Classification Search
CPC . G06F 19/3456; H04L 43/10; H04L 41/0213; G06Q 10/0633; G06Q 10/10; G06Q 50/22
USPC .......................................................... 705/2
See application file for complete search history.

(56) References Cited

U.S. PATENT DOCUMENTS

| | | | |
|---|---|---|---|
| 6,219,674 B1 | 4/2001 | Classen | |
| 6,952,695 B1 | 10/2005 | Trinks et al. | |
| 7,206,833 B1 * | 4/2007 | Sarangam | H04L 41/06 709/202 |
| 2002/0065683 A1 * | 5/2002 | Pham | G06F 17/30867 705/2 |
| 2005/0195077 A1 * | 9/2005 | McCulloch et al. | 340/500 |
| 2007/0226175 A1 * | 9/2007 | Resnic et al. | 707/1 |
| 2010/0235378 A1 * | 9/2010 | Armstrong | G06Q 10/10 707/769 |

* cited by examiner

*Primary Examiner* — Hiep V Nguyen
(74) *Attorney, Agent, or Firm* — Leason Ellis LLP

(57) ABSTRACT

Electronic capture of adverse event information includes selective input of adverse event information into a machine in response to prompt provided to the user based on a site visit. Such adverse event information is forwardable to a location over a communication link. The machine produces one or more alerts, if adverse event information has been input, after a prescribed period of time has transpired unless the machine is informed that the same information has already been forwarded to the location. In a preferred embodiment, the customer is a clinician. Optionally, received adverse event information can be parsed to audit whether any of the information, in fact, concerns an adverse event. Systems and software concerning related technological improvements are disclosed.

18 Claims, 3 Drawing Sheets

Fig. 2

```
                                          Home | Lists | Calls | Customer | Promo Order | Reports | Admin
      Day View | Week View | Calender | Call | Meeting | Time Off | Itinerary/Scheldule
      Cancel | Apply
          • Location  John Smith, 123 Lakeshore DR, Sparks,NV 89431 [v]  No Best Time for Friday: Click
      • Start Date Time 10/06/2006 [📅] 7:30 AM[v]  • End Time 8:00 AM[v]
          • Call Type Presentation [v]
      Accompanied By -Select Rep/DM/RM.[v] Tamper Prf. Scrip Pad#[        ]
          Sample Drop -Select-  [v]
               Status Open [v]
      YTD Amount Spent: $ 0
      Adverse Event/ Report of Concern/ Product Complaint or RSOP 1.7.1  Yes [v]

Next Appointment
      ─────────────────────────────────────────────────────────
      Next Appointment Date [        ] [📅] 8:00 AM[v]  End Time 8:30 AM[v]
      Next Appointment Type Appointment[v]

Products Presented
      ─────────────────────────────────────────────────────────
         First          Second            Third           Fourth
      OxyContin[v] | -Select Product-[v] | -Select Product-[v] | -Select Product-[v]

Notes
      ─────────────────────────────────────────────────────────

• Topics       [                              ]
       230↗             [ 0 of 1000                   ]

• Next Objective [                            ]
       240↗             [ 0 of 1000                   ]
                        Cancel | Apply
```

Adverse Event, ROC, Product Complaint, RSOP 1.7.1 Description

Reporter's Information
- Telephone: 775-555-1612  Fax: [ ]  ☐ Called-in ?
- E-Mail: [ ]

Patient's Information
- ● Sex: -Select-
- Initials: [ ]  DOB: [ ]  Age: [ ]
- ● Drug Product Name: -Select Product-
- ● Summary: [ ]
- 0 of 1000

} 220

Future Appointment Suggestions

| Customer Name | IMS Specialty | Line 1 Address | Line 2 Address | City | State |
|---|---|---|---|---|---|
| Jane Surgeon | AN | 2000 Terminal Way Ste. 165 | - | Reno | NV |
| Max Recovery | FM | 13 Pringle Way | - | Reno | NV |
| Norman O. Payne | OFA | 2020 Aitken St | - | Reno | NV |
|  |  |  |  |  |  |

ADVERSE EVENT DATA CAPTURE AND ALERT SYSTEMS AND METHODS

This patent application claims the benefit of priority under 35 U.S.C. § 120 of U.S. Non-Provisional application Ser. No. 11/925,403, filed on Oct. 26, 2007, entitled "Adverse Event Data Capture Software, Systems, And Methodologies," now U.S. Pat. No. 8,666,764, and under 35 U.S.C. § 119(e) of U.S. Provisional Application Ser. No. 60/867,923, filed on Nov. 30, 2006, entitled "Adverse Event Data Capture Software, Systems, And Methodologies," and of U.S. Provisional Application Ser. No. 60/863,243, filed Oct. 27, 2006, entitled "Territory Management System," which are hereby incorporated by reference in their respective entireties.

FIELD OF THE INVENTION

The present invention relates to the capture and reporting of adverse event information by field representatives of manufacturers and service providers, and, more particularly, to a software, systems and methodologies that assist in the capture and timely reporting of adverse event information.

BACKGROUND OF THE INVENTION

For several reasons, adverse events associated with medical and non-medical products need to be identified and reported. In the pharmaceutical sector, for example, safety testing typically goes through several phases prior to medicine being made commercially available, either as a prescribed medication or for over-the-counter consumer purchase. Indeed, safety studies are required for medical and related products such as drugs, biologicals, medical devices and cosmetics in order to receive approval from Federal agencies such as the Food and Drug Administration ("FDA") to release such products to market. However, vigilance in identifying safety issues continues throughout the market life of such products. Post-marketing vigilance, however, is less formal and normally involves voluntary reporting of potential adverse events by the professionals who become aware of an event. Manufacturers in the medical and pharmaceutical sectors are required to disclose true adverse events caused by their products to the FDA. However, because there can be uncertainty as to whether a given adverse event was caused by a product or not, investigations must be taken to explore the event with persons knowledgeable of the circumstances.

In one approach described in U.S. Pat. No. 6,952,695, a system manages the input of reported adverse event information using a hierarchically structured set of predefined terms to guide the user (presumably, a physician) in the data entry. The system of the '695 patent categorizes and characterizes the reported information and dynamically converts it into a standardized output that can be stored.

In many sectors including the pharmaceutical sector, field representatives have assigned territories and knowledge of the prescribing habits of the doctors and health care professionals in their territories and are in an advantageous position to capture and forward any adverse events to the pharmaceutical manufacturer for investigation and reporting, as appropriate. Tools are needed to assist field representatives in capturing any adverse event information that they may become of aware of in connection with a site visit to a physician, and to facilitate ensuring that such information is brought to the attention of the pharmaceutical manufacturer for investigation and reporting, as appropriate, in a timely manner. The present invention addresses this need and others.

SUMMARY OF THE INVENTION

In accordance with one aspect of the invention, a computer-assisted method for electronically capturing adverse event information that is known is provided which enables such information to be forwarded to another location by way of a communication link. The method includes steps that call for selectively inputting adverse event information in response to prompt. Any such adverse event information is forwarded to the location over the communication link. The machine into which this information has been input produces one or more alerts, if adverse event information has been input, if a prescribed period of time has transpired yet the machine has no indication that the adverse event information has been forwarded to the other location.

In further, optional aspects of the invention, received information in a call note can be parsed to audit whether any of the information, in fact, concerns an adverse event, and can be further processed by having the user confirm the findings of such an audit.

In a further aspect, the invention concerns a computer-readable medium which stores computer-executable instructions for causing a machine programmed thereby to the steps of prompting the user to enter adverse event information before completing a call note entry or before committing such an entry to a database, and forwarding any such input, adverse event information over a communication link. Further, the instructions cause the machine to produce one or more alerts if adverse event information has been input, each alert being produced after a time associated with receipt of the call note entry, in response to respective prescribed time periods transpiring prior to the forwarding step being performed.

In still a further aspect of the invention, a system for electronically capturing adverse event information known to a prescriber is described for forwarding such information to a location. The system comprises a first machine at the location and connectable to other machines through a communication link and a second machine having a processor and a database. The processor is configured to prompt a user to provide adverse event information before completing a call note entry or before committing such an entry to a database, to establish the communication link to the first machine at the location, and forward any received adverse event information to the first machine over the communication link; and to produce one or more alerts if adverse event information has been received, each alert being after a time associated with the receipt of the call note entry and being in response to respective prescribed time periods transpiring prior to forwarding of the adverse event information.

DESCRIPTION OF THE DRAWING FIGURES

FIG. 2 is a sample call notes entry form suitable for capturing adverse event information and other information from a representative's visit to a prescriber; and FIG. 2A is a continuation of the sample call notes entry form of FIG. 2, connected along match line A-A'.

DETAILED DESCRIPTION OF CERTAIN EMBODIMENTS

Figure 1:
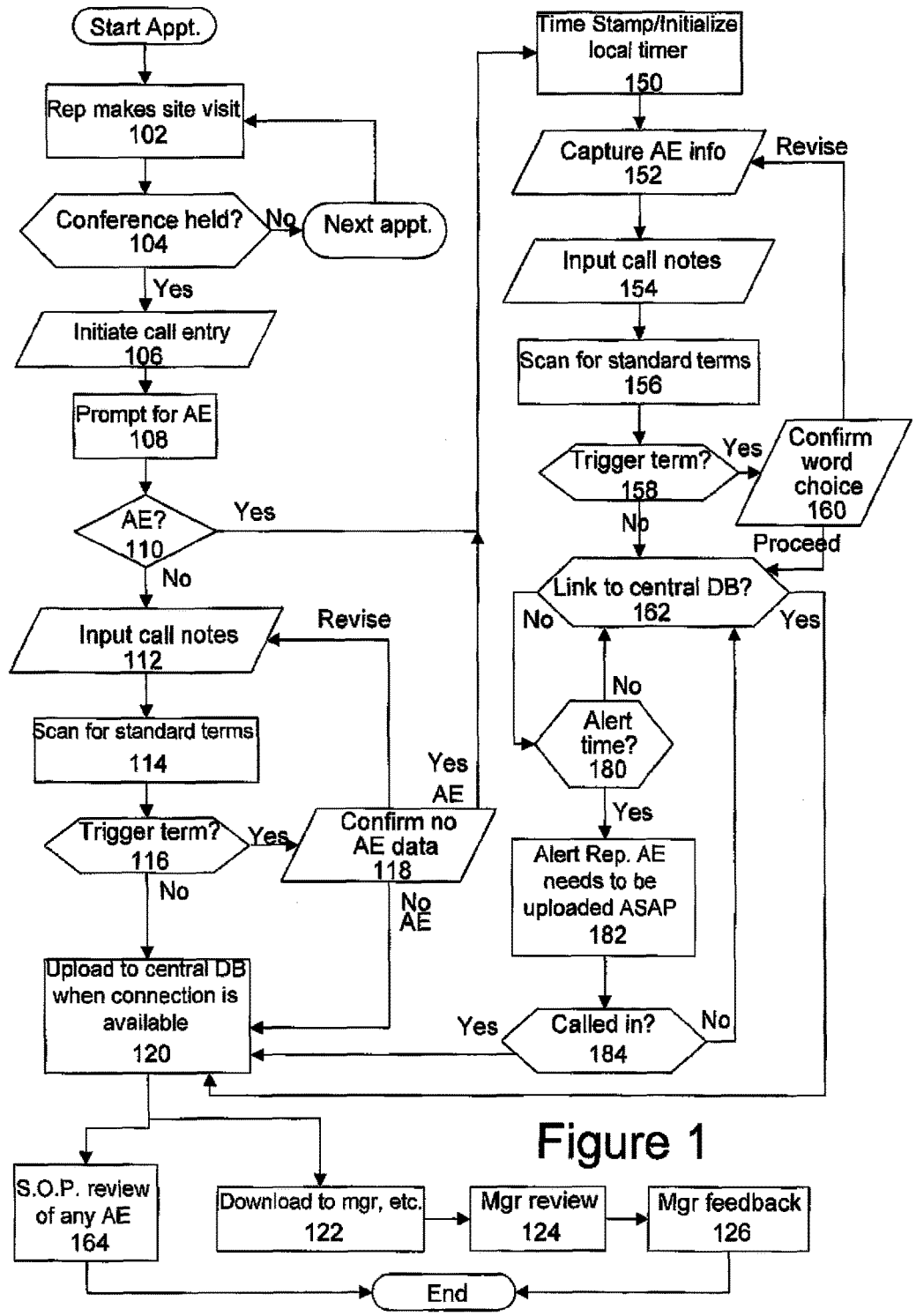
FIG. 1 is a flow diagram illustrating certain steps in accordance with one embodiment of the invention.

By way of overview and introduction, a territory management system provides representatives with a tool for conducting their activities in an efficient manner, and in particular includes functionality adapted to better ensure compliance with regulatory reporting requirements concerning adverse events and assists manufacturers in identifying and acting upon such information with warnings, product labeling and recalls.

The management system is preferably implemented as a software-based system, having components executing on a number of systems including a central computer and a multiplicity of remote machines, with each representative having a remote machine for his or her personal use and for forwarding adverse event information to a location associated with or accessible by the central computer. Without loss of generality, the present invention is described in relation to a particular representative using a single remote machine in the course of his or her activities covering an assigned territory. In the preferred embodiment described below, the representative is bespoke or contracted to a pharmaceutical manufacturer, and the representative "covers" a territory through visits to physicians and nurses (more generally, "prescribers") at which the representative is able to discuss and promote the use of the manufacturer's products.

A preferred software tool for territory management is described in the aforementioned U.S. Provisional Application Ser. No. 60/863,243. This software provides through a Web-browser interface a number of tools that assist the representative in planning, recording, and tracking activities with clinicians (which generally include prescribers, medical assistants, pharmacists) or customers, as the case may be. This software also includes features that assist a representative with compliance issues concerning certain state or federal requirements (e.g., limits and restrictions concerning gifts to health care professionals), and can assist in reducing discrepancies in sample inventories as between stored and on-hand inventories. Various features of this software are described in other patent applications, now co-pending.

Referring now to FIG. 1, a flow diagram illustrates functionality suitable for capturing adverse event (AE) information that a representative may learn about in the course of covering his or her territory. Because the representative makes a point of visiting prescribers he or she may be the first person to learn of an event concerning a patient's use of a particular pharmaceutical. Likewise, in other fields, the representative can learn of a strain, performance change, part failure, and the like concerning a product, machine, system, process, or software concerning the subject matter that the representative represents, and for ease of discussion all such developments are referred to as "adverse events."

The process illustrated in FIG. 1 concerns an appointment of the representative, which can be a scheduled appointment or a "drop-in" visit. In the area of pharmaceutical representation, it is common for a representative to drop-in on a prescriber within the representative's assigned territory with the hope that the prescriber will be able to speak with the representative for a few minutes. The nature of such visits can vary from informal to formal, but one objective of the representative is to promote a prescriber's familiarity and understanding of pharmaceuticals that the representative wishes the prescriber to prescribe to patients. In other fields, the representative similarly has an objective of promoting purchase and use of his or her represented products and services through educational and promotional efforts.

Thus, at block 102, the representative makes a site visit to a particular prescriber's office. The representative typically makes a number of visits during the course of a day, whether scheduled or drop-in, and these visits can be coordinated through a calendar function provided by the same programmed system that handles a representative's reporting of newly disclosed adverse event information. The scheduling and calendar functions form no part of the present invention.

In the event that the prescriber is not available, for a conference with the representative, as conceptually indicated by the test at block 104, the representative goes to a next appointment by traveling to another site within his or her territory, preferably with guidance from a calendared set of appointments that fill the day. If, however, a conference is held with a prescriber at a particular site visit, then the representative is supposed to capture a summary of who was met, what products (services) were discussed, whether samples were provided (and details concerning same), and propose a next meeting and follow-up discussion points.

Representatives generally seek to satisfy any concerns expressed by the clinicians in their territory, and so follow-up points can be captured in the territory management software so that the representative can better address those concerns with their clinicians. However, representatives also have an obligation to the company they represent to document any reported adverse events as those events might require further investigation or follow-up, and for at least some adverse events have a legal obligation to report such events within a limited window of time after learning of the event, such as within 48 hours.

Use of the territory management system commences then at block 106 at which the representative initiates the entry of visitation notes, known as making a "call completion" because he or she has completed a sales call to the clinician/customer and has meeting notes to record. The user can initiate this data entry process in a variety of ways. For example, from a calendar feature of the management system an icon such as a telephone icon can be selected to bring up a call notes entry form. Alternatively, the calendar feature of the management system can include entries showing the time, location, or both of the visits for that day which the representative can select to bring up the call-notes entry form. Yet another alternative is that the representative can call up a prescriber summary page which can include a link (or an icon as mentioned above) to enter call notes that are to be associated with that prescriber visit.

Preferably, prior to enabling entry of the call notes, the software prompts the representative (user) through the interface at block 108 as to whether he or she was informed of any adverse event information during the course of the site visit, including, by way of examples, an adverse event, a report of concern ("ROC"), a product complaint, or other information that satisfies a standard operating procedure for reporting such events. The field-capture of such information is of vital importance to the pharmaceutical sector, and can be important in other sectors as well, and so in a preferred implementation, an alert such as a dialog box is presented to the user to confirm whether any such information was discussed during the conference with the prescriber. The alert can require an affirmative response by the user to expose or cause the call-notes entry form to be presented. Thus, for example, the alert can be a conventional dialog box with a text string requesting whether such information was discussed and two buttons, one "yes" and one "no". After receiving the user's response, the call-notes entry form can be presented with a selection list populated with the value selected by the user (and optionally changeable during the course of call-notes data entry). Alternatively, the adverse information prompt can comprise fields within the call notes entry form without the use of, a separate alert or dialog box. Regardless of the form for the prompt, it is preferably provided prior to the call notes entry form being completed, for example, before it is committed (written to) to the local database.

At block 110, a test is made to determine the value input by the representative in response to the prompt from block 108. Of course, if the prompt was not provided at this stage, no test is required. The user can selectively input adverse event information, depending on whether he or she has such information to be captured. In the event that the user indicates that an AE was discussed (block 110: "YES"), then the process flow branches to block 150, discussed below, with the software responding to the user input with steps that affirmatively capture and forward a minimum set of required information to a central machine. If the user indicates that there is no adverse event information to report, then the user can proceed to input call notes through the call-notes entry form, at block 112. An exemplary call-notes entry form 200 is shown in FIG. 2.

Among a variety of fields that can be provided, typically there are certain data fields which are set for required data entry in order for the form completion to be validated. Region 210 includes a variety of fields for call note capture, including certain required, data-fields indicated with highlighted marks next to them (e.g., Location, Start date time, etc.). Several of the data fields are preferably populated with information directly from the representative's calendar. Thus, if the call notes are in furtherance to a calendared visit, the particular prescriber, his or her address, start time, end times, and the call type can all be known from the calendar entry. Among the data-fields provided, the representative can indicate whether a sample was dropped off (as well as other details as described in U.S. Provisional Application Ser. No. 60/867,903, filed on Nov. 30, 2006, entitled "Inventory Control over Pharmaceutical Sample Distributions, Software, Systems and Methodologies"), input a next appointment which entry can populate the representative's calendar. In addition, there are preferably selection lists that permit ready identification of which products were presented to the prescriber, and free-text fields in which the representative identifies the discussion topics and any objectives for follow-up at a next visit. The topics text box 230 and the next-objective text box 240 are two free text fields which can hold, for example, up to 1000 characters. Briefly, region 220 includes fields that are specific to the capture of adverse event information and is discussed below.

Optionally, the call notes entry form can inform the representative of the year-to-date spending on that health care professional. This can assist the representative in staying in compliance with state limits on gifts to individual health care professionals, as described in application Ser. No. 60/867,906, filed on Nov. 30, 2006, entitled "Pharmaceutical Representative Expense Management Software, Systems, and Methodologies," and is particularly beneficial when more than one representative from the same manufacturer has paid a call to that prescriber, directly or indirectly by visiting the same hospital or medical group and having apportioned expenses to that same prescriber.

Referring again to FIG. 1, when the representative seeks to apply the data in the call entry form to the local database on the machine he is using (e.g., a laptop computer or personal digital assistant), validation rules can execute to monitor and flag any entries for their respective levels of completion, format, spelling and even content, to better ensure that good data is being captured. Thus, for the free-text fields, a minimum of five characters might have to be entered to result in form validation. Among the validation rules, at block 114, the content of the free text fields can be compared against a dictionary or thesaurus of standard terms that might be probative of an AE in-fact. For example, the representative might have documented in the topics field 230 a discussion of "pain" or "ache" which the dictionary might associate with a likelihood of an AE in-fact. In the event that a trigger term is found within the free-text fields, as determined at block 116, then the representative can be asked to confirm that the term is not, in fact, associated with an adverse event (in this flow branch, the representative indicated AE? NO at block 110). If the representative confirms that the term in the free text field that triggered this audit inquiry was not an adverse event, process flow proceeds to block 120 at which time the completed call notes are uploaded to a central database. On the other hand, the representative might wish to revise his word choices as a result of this automated audit inquiry, in which case process flow returns to block 112 so that the call notes can be revised. Still another possibility is that the representative reconsiders his prior indication of no AE and in that case the process flow proceeds to block 150.

If there are no adverse events to report, then the call notes, once uploaded to the central database can be downloaded to a manager's machine, as indicated at block 122. For example, to the machine of a district manager whose responsibility is to supervise and review the work of one or more representatives in one or more territories. Once the call notes have been downloaded to the manager's machine, the manager can review the call notes as well as the productivity of the representative (block 124) and can provide feedback (block 126), as appropriate. The process of FIG. 2 generally ends at that point with respect to a particular call note; however, the representative may make any number of site visits and enter any number of call notes for each such visit prior to the upload at block 120, and the time frame for download, review and feedback by a manager, if any, can be entirely different than the time frame of the events leading to those final steps.

In the event that the representative's machine includes a wireless network capabilities (e.g., a broadband card that can connect the machine through a "hot spot"), the upload at block 120 can occur whenever the system detects that it has secure network connectivity, and this process can be performed as a background thread while the user performs other tasks on the machine running the territory management software.

The upload to the central database requires a communication link between the central computer and the remote machine of the representative. The upload is preferably conducted in accordance with U.S. Provisional Application Ser. No. 60/867,943, filed on Nov. 30, 2006, entitled "Data Cache Techniques In Support Of Synchronization of Databases In A Distributed Environment," which is hereby incorporated by reference in its entirety. During the same communication session, the central machine can download information to the representative's machine, but such downloads are not pertinent to the present invention. Downloads can be to revise the scope of the representative's territory, to provide prescription-writing information on the prescribers in the representative's territory, to add new prescribers, and to change the user's role (e.g., from representative to district manager). Such downloads are preferably conducted in accordance with U.S. Provisional Application Ser. No. 60/867,945, filed on Nov. 30, 2006, entitled "Software, Systems and Methodologies For Realignment of Remote Databases By A Central Database In Support of Field Representative Territory Assignments," which is hereby incorporated by reference in its entirety.

Referring now to block 150, in the event that the representative has indicated that he has AE information to input, the time of the visit is captured and used to initialize a local timer on the representative's machine. The time of this event can be taken from one of the fields of the call notes entry form, such as the start date/time or the end date/time fields. Alternatively, the machine can make a call to its system clock and use that time as the basis for the local timer. The purpose of the local tinier is to provide an alert to the representative in the event that a prescribed period of time has elapsed yet the system has not been informed that the AE information has been communicated. As noted above, it is important that such information be promptly communicated to the manufacturer so that there is sufficient time to investigate the circumstances and determine an action, which could include informing a third-party pharmacovigilance community, the Food and Drug Administration, or foreign agencies with similar purposes.

At block 152, the AE information is captured in the region 220 of the call notes entry form, shown in FIG. 2A. This region includes fields that can be pre-populated with information if available from the local database used by the software on the representative's machine. Thus, for example, the telephone and fax numbers and email address of the prescriber who was visited can be pre-populated, if that information is already known. The minimum information to be provided in call notes entry form 200 is the sex (male or female) of the patient, the product that was taken which is attributed to being associated with the AE, and a free-text summary field (e.g., up to 1000 characters) to describe the symptoms and circumstances of the event. Because AE information is patient specific, it is preferable to capture a sufficient amount of information to ensure not only that a suitable assessment can be made regarding the reported event, but also to better ensure that the record can be identified as a duplicate in the event that the event has been separately reported. In this regard, the patient's initials, age, and date of birth can be captured as well if that information is provided.

Independent of this data entry, the representative can, and is encouraged to, call in the AE information, which can be indicated in a suitable check-box provided within the region 220.

The user completes AE information entry with an "apply" button to apply the newly entered information to the local database. Likewise, the user inputs call notes, as described above in connection with block 112.

At block 156, a scan of the content of the free text summary field is preferably performed for comparison against a reference such as a dictionary of terms (e.g., the same dictionary as used at block 114 or a different dictionary) that might present ambiguity or otherwise be flagged as raising questions upon a later review. For example, the use of the term "pain" or "ache" without the use of a noun identifying the place of pain or ache could trigger, at block 158 that the representative's word choice is not ideal. Alternatively or in addition, the comparison at blocks 113 and 156 can be to a rule base, such as one that parses the text box for ambiguities or informalities due to grammar or one that parses the text box for particular words or for identifying certain frequently used terms by that representative. In the event of such a trigger, the user can confirm his or her word choice at block 160, by either indicating a desire to revise the text entries, in response to which the software loops back to blocks 152 and/or 154, or by indicating that the entries are acceptable. If the entries entered in the call notes and the adverse event free-text summary field are deemed to be acceptable to the user, or if no trigger terms were identified, process flow proceeds to block 162.

After the entry of data and commitment to the local database on the user's machine, a test is made at block 162 whether the representative's machine can establish a communication channel to the central database. This step precedes the upload at block 120, and, as noted above, is typically a background process but can be attempted in response to a user request, through the software's user-interface, to establish such a connection. The test as to whether there has been a connection to the central database has particular pertinence, however, with regard to the handling of the AE information. In particular, if no link can be established within a prescribed alert time, as tested at block 180, an alert is preferably provided to the representative at block 182 that the AE information must be uploaded as soon as possible, or otherwise relayed to the manufacturer. Thus, for example, alerts can be programmed to display to the user two hours after the site visit, again at four hours after the site visit, and each hour after that. Such programming causes the representative's machine to issue alerts in response to the expiration or transpiration of the prescribed alert times. Also, the alert to relay the AE information can block other functionality of the representative's machine (or at least of the territory management software) until the alert condition has been satisfied. One possibility is that the representative may indicate at block 184 that he or she has "called in" the data (see the filled-in check box in region 220), which may qualify as a basis for removing the alert, or optionally for reducing the frequency of requesting that an upload communication session be established. In that case, the AE information has already been forwarded to the designated location independently of the use of the representative's machine, yet follow-up notifications asking the representative to confirm that the information was called in can still be provided. However, if the AE information has not been "called-in," and no link has been established, the alerts will preferably continue. On the other hand, if the link is established (or at some time after the information has been called in), the completed call note entry forms and other information are uploaded onto the central database, at block 120, and that information is available for manager handling at blocks 122, 124 and 126, as previously described.

In addition, at block 164, after uploading to the central database, the manufacturer or an agent thereof implements a standard operating procedure by which the AE information is reviewed. That review is understood by those of skill in the art, but generally includes one or more of the following actions: an assessment of the reported data itself and against other reports and information that are available; a call to the representative for more details on the call to the prescriber; a call to the prescriber for further information on how the event transpired and on the subject patient; a notification to a third-party such as a pharmacovigilance community, the Food and Drug Administration or a foreign agency with a similar role or purpose.

In the foregoing description, certain flow diagrams have been shown and processes described in relation to those flow diagrams which provide a reference for discussion purposes. In an actual implementation of the methods of the present invention, the steps can comprise event-driven routines that can run in parallel and can be launched and executed other than as shown by the simple depiction in the flow diagrams.

Accordingly, it is the performance of the steps recited in the claims appended below which is pertinent, and not the order of operation of the steps themselves.

We claim:

1. A computer-assisted method for electronically capturing adverse event information in order for said information to be forwardable to a first machine at a location by way of a communication link, comprising the steps of:
   providing a user with at least one adverse event information prompt within a territory management software using instructions executing in a processor of a second machine;
   receiving as an input to the second machine adverse event information from the user;
   testing whether a connection over a communication link to the first machine at the location has been established, using programming executing in the processor;
   in the event that the communication link has been established, forwarding the input adverse event information to the first machine over the communication link; and
   after the input is received at the second machine, and in the event the communication link has not been established, and prior to the forwarding step being performed:
      initializing a local timer at the second machine using programming executing in the processor, the local timer having a prescribed alert time;
      producing one or more alerts to the user at the second machine in response to the expiration of the prescribed alert time using programming executing in the processor that the adverse event information must still be forwarded to the first machine; and
      blocking functionality of the territory management software at the second machine to which the user otherwise has access in the absence of the produced alerts, using programming in the processor concerning the production of the one or more alerts, until the input adverse event information has been forwarded to the first machine over the communication link.

2. The method of claim 1, further comprising entering into the second machine a note concerning a visit by the user, and identifying to the second machine that the forwarding step has been performed by associating a called-in status with the note.

3. The method of claim 1, wherein the performance of the forwarding step is indicated by a filled-in check-box among the input adverse event information.

4. The method of claim 1, further comprising entering into the second machine a note concerning a visit by the user, and comparing any input adverse event information, the entered note, or both, against a reference and selectively prompting the user to confirm said information.

5. The method of claim 1, further comprising entering into the second machine a note concerning a visit by the user, wherein the step of providing the at least one adverse information prompt is prior to the note being completed.

6. The method of claim 1, wherein the step of providing the at least one adverse information prompt includes the step of presenting a dialog box on a screen of the second machine, and wherein at least one of the prompts requires a response to be input to the second machine in order to close the dialog box.

7. The method of claim 1, including the additional step of comparing any input adverse event information against a reference and selectively prompting the user to confirm said information.

8. The method of claim 1, further comprising entering into the second machine a note concerning a visit by the user, wherein the forwarding step further includes forwarding the note to the location over the communication link.

9. The method of claim 1, wherein the one or more alerts produce an alert condition, further comprising blocking functionality of software at the second machine until the alert condition has been satisfied.

10. The method of claim 1, wherein blocking functionality of the territory management software at the second machine comprises blocking functionality of the application program at the second machine.

11. A non-transitory computer-readable medium storing computer-executable instructions for causing a first machine programmed thereby to:
   provide a user with at least one adverse event information prompt within a territory management software using instructions executing in a processor of the first machine;
   receive as an input to the first machine, adverse event information from the user;
   test whether a communication link to a central machine has been established, using programming executing in the processor;
   in the event that the communication link has been established, forward the input adverse event information to the central machine over the communication link; and
   after the input is received at the first machine, and in the event the communication link has not been established, and prior to any forwarding:
      initialize a local timer at the first machine using programming executing in the processor, the local timer having a prescribed alert time;
      produce one or more alerts to the user at the first machine in response to the expiration of a prescribed alert time using programming executing in the processor that the adverse event information must still be forwarded to the central machine; and
      block functionality of the territory management software at the first machine to which the user otherwise has access in the absence of the produced alerts, using programming in the processor concerning the production of the one or more alerts, until the input adverse event information has been forwarded to the central machine over the communication link.

12. The non-transitory computer-readable medium of claim 11, wherein the prescribed alert time is obtained from a system clock of the first machine.

13. The non-transitory computer-readable medium of claim 11, further storing computer-executable instructions for causing the first machine programmed thereby to enter into the first machine a note concerning a visit by the user, wherein the prescribed alert time is commenced with the entry of the note into the first machine.

14. The non-transitory computer-readable medium of claim 11, wherein the computer-executable instructions cause the first machine to programmed thereby to block functionality of the application program at the second machine.

15. A system for electronically capturing adverse event information known to a prescriber for forwarding to a location, comprising:
   a first machine at the location and connectable to other machines through a communication link;
   a second machine having a processor, the processor being configured by instructions executing in the processor to:

provide a user with at least one adverse event information prompt within a territory management software using instructions executable in a processor of the second machine;

receive as an input to the second machine, adverse event information from the user;

test whether a communication link to the first machine at the location has been established using programming executing in the processor;

in the event that the communication link has been established, forward the input adverse event information to the first machine over the communication link; and after the input is received at the second machine, and in the event the communication link has not been established, and prior to any forwarding:

initialize a local timer at the second machine using programming executing in the processor, the local timer having a prescribed alert time;

produce one or more alerts to the user at the second machine in response to the expiration of the prescribed alert time, using programming executing in the processor, that the adverse event information must still be forwarded to the first machine; and block functionality of the territory management software at the second machine to which the user otherwise has access in the absence of the produced alerts, using programming in the processor concerning the production of the one or more alerts, until the adverse event information has been forwarded to the first machine over the communication link.

16. The system of claim 15, wherein the prescribed alert time is obtained from a system clock of the second machine.

17. The system of claim 15, wherein the processor of the second machine is further configured by instructions executing therein to enter into the second machine a note concerning a visit by the user, wherein the prescribed alert time is commenced with the entry of the note into the second machine.

18. The system of claim 15, wherein the processor of the second machine is further configured by instructions executable therein to block functionality of the application program at the second machine.

* * * * *